United States Patent
Kluijtmans et al.

(10) Patent No.: US 7,803,771 B2
(45) Date of Patent: Sep. 28, 2010

(54) RECOMBINANT GELATIN PARTICLES FOR CELL ADHESION

(75) Inventors: Sebastianus Gerardus Johannes Maria Kluijtmans, Zeist (NL); Jan Bastiaan Bouwstra, Bilthoven (NL)

(73) Assignee: Fujifilm Manufacturing Europe B.V., Tilburg (NL)

( * ) Notice: Subject to any disclaimer, the term of this patent is extended or adjusted under 35 U.S.C. 154(b) by 185 days.

(21) Appl. No.: 12/158,018

(22) PCT Filed: Dec. 22, 2006

(86) PCT No.: PCT/NL2006/050326

§ 371 (c)(1),
(2), (4) Date: Jun. 18, 2008

(87) PCT Pub. No.: WO2007/073190

PCT Pub. Date: Jun. 28, 2007

(65) Prior Publication Data

US 2009/0246282 A1      Oct. 1, 2009

(30) Foreign Application Priority Data

Dec. 23, 2005   (EP) ................................... 05112965

(51) Int. Cl.
*A61K 38/00*   (2006.01)
*C07K 1/00*    (2006.01)
(52) U.S. Cl. .......................................... 514/12; 530/350
(58) Field of Classification Search ................. 514/12; 530/350
See application file for complete search history.

(56) References Cited

FOREIGN PATENT DOCUMENTS

| | | |
|---|---|---|
| GB | 1013577 A | 12/1965 |
| WO | WO 97/40701 A | 11/1997 |
| WO | WO 03/079805 A | 10/2003 |
| WO | WO 03/104313 A | 12/2003 |

*Primary Examiner*—Maryam Monshipouri
(74) *Attorney, Agent, or Firm*—Gilberto M. Villacorta; Sunit Talapatra; Foley & Lardner LLP

(57) ABSTRACT

The present invention relates to cell carrier particles prepared from recombinantly produced gelatins comprising at least two outer lysine residues which are separated by at least 25 percent of the total number of amino acids in the recombinant gelatin polypeptide. The invention is also directed at applications in which such cell carriers are used, for example as injectable cell carrier, for tissue augentation or cosmetic surgery or as microcarrier in in vitro cell cultivation.

23 Claims, No Drawings

RECOMBINANT GELATIN PARTICLES FOR CELL ADHESION

This application is a 371 of PCT/NL06/50326 filed Dec. 22, 2006, which claims priority to European patent application EP 05112965.8 filed Dec. 23, 2005

FIELD OF THE INVENTION

The invention relates to cell carrier particles prepared from gelatins. More specifically the invention is directed to such particles prepared from recombinantly produced gelatins. The invention is also directed at applications in which such cell carriers are used, for example as injectable cell carrier, for tissue augmentation or cosmetic surgery or as microcarrier in in vitro cell cultivation.

BACKGROUND

It is well known that many animal cells need to be anchored to a surface in order to grow. Cells requiring surface attachment are for example keratinocytes, fibroblasts, myocardiocytes, ovary cells, hepatocytes, Langerhans islets.

In many medical applications a matrix is provided to which cells can adhere thus facilitating cell growth. For example in treatment of burn wounds or other open wounds sheet materials on which keratinocytes and/or fibroblasts are grown are used as skin replacements as described in for example WO 00/29553.

Cell supports are used in a variety of applications in which cell attachment is important for proliferation of the cells. Gelatin is a well known substrate for cell attachment. It is used as a coating on carrier materials such as polystyrene or glass particles for cell culturing. Application of gelatin as a scaffold in tissue engineering or as a coating of implant materials is also known. In most cases the gelatin is crosslinked. However, gelatin has several drawbacks. Being from a natural source the composition is in principle undefined, and contaminations such as proteins, viruses and prions may be present requiring further measures to guarantee biocompatibility.

WO 2005/079879 describes a process for producing cell carrier or medical material consisting of crosslinked collagen fibers. Crosslinked gelatin layers are also used to coat implants. WO 00/6701 describes the use of gelatin scaffolds for cell adhesion in repairing myocardial scar tissue or for coating pacemakers.

For in vitro cultivation of cells such as for example yeast cells or animal cells, carriers are used that provide a surface for cell-attachment. The cell-binding properties of such surfaces can be enhanced by coating with gelatin, or the carrier may consist of crosslinked gelatin particles.

EP 0 222 718 describes macroporous particles that are suitable as microcarriers for cultivation of anchor-dependent cells, but is silent with respect to properties other than macroporosity. Preparation of gelatin microcarriers is described in for example WO 90/13625, SU 1724687, WO 02/48247 and WO 03/104313.

SUMMARY OF THE INVENTION

It is an object of this invention to provide gelatin based cell carriers with uniform physical and (bio)chemical properties such as biodegradability and cell attachment.

It is also an objective of this invention to provide such cell carriers with a uniform performance in applications in which attached cells contribute to a tissue repairing or healing process or in in vitro cell cultivation processes.

It is further an objective of this invention to provide such gelatin based cell carriers having an improved cell attachment.

It is also further an object of this invention to provide cell carriers that have no risk of viral infections, are free from contaminations that pose a health risk and have a reduced immunogenicity.

These objects were achieved by a cell carrier particle comprising crosslinked recombinantly produced gelatin polypeptides, wherein said recombinantly produced gelatin polypeptides comprise at least two lysine residues, said lysine residues being extreme lysine residues wherein a first extreme lysine residue is the lysine residue that is closest to the N-terminus of the polypeptide and the second extreme lysine residue is the lysine residue that is closest to the C-terminus of the polypeptide and said extreme lysine residues are separated by at least 25 percent of the total number of amino acids in the recombinant gelatin polypeptide.

It is a great advantage of the cell carriers of this invention that uniform cell carriers can be produced in which the degree of cell attachment and the degree of crosslinking can be tuned or tailor made by regulating the presence of factors such as lysine residues, further amino acids for crosslinking with lysine residues, glycosylation and the presence of the specific cell binding sequences such as the amino acid sequence—arginine-glycine-aspartic acid—(herein referred to as RGD-motifs). It is also an advantage that all particles made from one type of recombinant gelatin have comparable properties.

DETAILED DESCRIPTION

Natural gelatins have several drawbacks. Besides the well known risk of prion contamination the material has an undefined molecular weight due to its natural origin and due to its preparation method. A gelatin with a given average molecular weight has a broad molecular weight distribution. Methods like ultracentrifugation can separate a naturally produced hydrolyzed gelatin in a higher and a lower weight fraction, but each fraction will have a broad size distribution. Higher molecular weight fractions such as higher than 50 kiloDalton (kDa) may contain larger structures of up to 200 kDa or 300 kDa. Lower molecular weight fractions of for example less than 50 kDa will contain smaller molecules of less then 5 kDa, or less than 1 kDa, or even smaller. By crosslinking such natural gelatins or collagens, cell carrier particles can be formed, however, too large particles may form when crosslinking high molecular weight gelatin fractions, and too small particles may form when crosslinking low molecular weight gelatin fractions.

It is preferred to have a uniform cell carrier particle size, since this results in a uniform cell density in in vitro cell culture applications and in medical applications. Too large particles will bind less cells relative to their volume, and are therefore less effective. Too small particles will bind no cells and are therefore unproductive. We found that a gelatin based cell carrier with a uniform particle size distribution, uniform physical and (bio)chemical properties and uniform behavior can be made by using a recombinant gelatin that comprises at least two outer (also referred to as extreme) lysine residues separated by at least 25% of the total number of amino acids in the recombinant gelatin polypeptide. In a preferred embodiment the recombinantly produced gelatin polypeptide comprises at least one lysine residue between the outer (extreme) lysine residues.

In a further preferred embodiment of the present cell carrier particles the recombinantly produced gelatin polypeptides comprise at least two amino acid residues, said two amino acid residues being extreme amino acid residues, which independently are selected from an aspartic acid residue and a glutamic acid residue, wherein a first aspartic acid residue or glutamic acid residue is the aspartic acid residue or glutamic acid residue that is closest to the N-terminus of the polypeptide and the second extreme aspartic acid residue or glutamic acid residue is the aspartic acid residue or glutamic acid residue that is closest to the C-terminus of the polypeptide and said extreme aspartic acid residues and/or glutamic acid residues are separated by at least 25 percent of the total number of amino acids in the recombinant gelatin polypeptide. In yet a further embodiment the recombinantly produced gelatin polypeptides comprise at least one aspartic acid residue or glutamic acid residue between said extreme extreme aspartic acid residues and/or glutamic acid residues.

Gelatins or collagens can be crosslinked via the amine groups of lysine, via carboxyl groups of glutamic acid or aspartic acid, or a combination thereof. Suitable crosslinking agents are preferably those that do not elicit toxic or antigenic effects when released during biodegradation. Suitable crosslinking agents are, for example, one or more of glutaraldehyde, water-soluble carbodiimides, bisepoxy compounds, formalin, 1-ethyl-3-(3-dimethylaminopropyl) carbodiimide, bis-hydroxy-succinimides, glycidyl ethers such as alkylene glycol diglycidyl ethers or polyglycerol polyglycidyl ether, diisocyanates such as hexamethylene diisocyanate, diphenylphosphorylazide, D-ribose. Crosslinking techniques are also described by Weadock et. al. in Evaluation of collagen crosslinking techniques (Biomater. Med. Devices Artif. Organs, 1983-1984, 11 (4): 293-318). In a preferred embodiment water-soluble 1-ethyl-3-(3-dimethylaminopropyl) carbodiimide (EDC) is used.

Other suitable crosslinking agents are triazines such as for example dichlorohydroxy-triazine. Other crosslinking compounds are divinyl sulfones, di-anhydrides, bifunctional imidates di-epoxides or dimaleiimidines. It is also possible to use bi-functional crosslinking compounds that have different active groups such as a bifunctional crosslinking compound comprising an epoxyde and an anhydride in one molecule.

Also useful are enzymatic crosslinking compounds such as trans-glutaminase.

Also crosslinking compounds that can attach to more than 2 crosslinkable amino acid residues such as for example lysine residues can be applied such as for example cyanuric chloride. In that respect compounds that combine three or more reactive groups are envisaged such as a compound comprising two epoxide- and an anhydride group.

In one embodiment crosslinking of the collageneous polypeptide is achieved by addition of one or more crosslinking agents. These comprise agents that start crosslinking spontaneously upon addition to collageneous polypeptide solution, or after adjusting for example, pH, or by photo initiation or other activation mechanisms.

A well known crosslinker that is considered to be biocompatible is for example glutaraldehyde, which crosslinks two lysine residues. Another well known biocompatible crosslinker is EDC, which couples an amine and a carboxyl group.

To contribute to particle formation, the recombinant gelatin comprises at least two lysine residues. Preferably the recombinant collagen polypeptide comprises at least 3, or at least 4, 5, 6, 7, 8, 9, 10, 11 or at least 12 lysine residues. In a further embodiment the recombinant gelatin polypeptide comprises in addition to the lysines also at least two amino acid residues selected from aspartic acid and glutamic acid, more preferably the recombinant gelatin polypeptide comprises at least 3, or at least 4, 5, 6, 7, 8, 9, 10, 11 or at least 12 aspartic acid and glutamic acid residues.

For contributing to the three dimensional network structure the lysines, aspartic acid and/or glutamic acid residues should have a spatial distribution over the polypeptide. Thus in one embodiment each stretch of 50 amino acids comprises at least 1, preferably at least 2, lysine residues or at least 1, preferably at least 2, aspartic acid or glutamic acid residue or at least 1 lysine residue and at least 1 aspartic acid or glutamic acid residue. Preferably each stretch of 40 amino acids comprises at least 1 lysine residues and/or at least one aspartic- or glutamic acid residues, even more preferably each stretch of 25 amino acids.

Preferably the crosslinkable amino acid residues are not adjacent to each other. More preferably they are separated by at least 5 amino acids, more preferably by at least 10 amino acids.

Especially in case of recombinantly produced gelatin, the number of lysine residues can be increased as desired. Many crosslinking agents bind to lysine residues and/or N-terminal amines. Natural gelatins contain 25 to 27 lysine residues and 112-133 glutamic- and aspartic acid residues per 1000 amino acids. In recombinant gelatins the number of lysines can be reduced to for example equal to or less than about 20, 15, 10 or 5 lysines per 1000 amino acids or increased to for example equal to or more than about 30, 40 or 50 lysines per 1000 amino acids. The number of glutamic- or aspartic acid residues can be decreased to for example equal to or less than about 100, 90, 80, 70, 60, 50, 40, 30, 20, 10 or 5 residues per 1000 amino acids or can be increased to for example equal to or more than 150 residues per 1000 amino acids.

When a part of a human collagen sequence is expressed, both asparagine and aspartic acid and both glutamine and glutamic acid may be present in the recombinant polypeptide. When desired, the glutamine and asparagine residues can be de-aminated, converting them to aspartic acid and glutamic acid residues.

In one embodiment the recombinant gelatin of the cell carrier particles is crosslinked by adding between 0.02 and 1.0 millimol crosslinking compound(s) per gram recombinant gelatin. Thus, the cross-linking compound(s) may be present in an amount of about 0.02, 0.05, 0.1, 0.25, 0.5, 0.6, 0.7, 0.8, 0.9 or 1.0 millimol/gram gelatin. In another embodiment the cell carrier particles are crosslinked by adding between 0.5 and 5.0 millimol crosslinking compound(s) per gram recombinant gelatin (or radiation induced crosslinking which is equivalent hereto), preferably about 1.0 to 2.5 millimol/g. Thus, the cross-linking compound(s) may be present in an amount of about 0.5, 0.6, 0.7, 0.8, 0.9, 1.0, 2.0, 3.0, 4.0 and 5.0 millimol/gram recombinant gelatin. In yet another embodiment the recombinant gelatin is crosslinked by adding between 0.25 and 2.5 millimol crosslinking compound(s) per gram gelatinous polypeptide.

Thus, the number of crosslinkable amino acid residues together with the amount of crosslinking compound that is applied can be used to determine or customize the physical properties of the recombinant collagen particles. A high number of crosslinkable residues and/or a high concentration of crosslinking compound can yield particles that are suitable for cell cultures, in which the particles are subjected to mechanical stress. Lower numbers of crosslinkable amino acid residues and/or low concentrations of crosslinking compounds can yield particles that are easily deformable and can be applied for injectable collagen particles for medical or pharmaceutical applications.

In one embodiment the crosslinking agent is added to the gelatin during preparation of the cell carrier particles. In another embodiment particles are formed, and crosslinking compound is added during the final stage of particle formation or after particles have been formed, to produce particles that are surface-crosslinked, but have essentially no internal crosslinking.

Recombinant production of gelatin makes it possible to obtain a monodisperse molecular weight distribution and also a uniform amino acid composition of the gelatin polypeptides. When hydrolyzing natural gelatin for preparing crosslinked cell carrier particles, low molecular weight fractions can be present that contain none or only one lysine residue, or a cluster of lysine residues that are too close together to effectively contribute to crosslinking. Such structures do not contribute to the formation of particles. It is likely that many low molecular weight fractions from natural gelatins do not have the amino acid sequence arginine-glycine-aspartic acid (-RGD-) which may be advantageous required for cell attachment. So, even if a small cell carrier particle is formed it may not contribute to cell attachment. In cases where the absence of an RGD-motif is preferred, a skilled person may be hesitant to use natural gelatins. Recombinantly produced collagens that do not comprise the RGD sequence can be applied in that case.

Because of the variation in particle size, amino acid composition and hence degree of crosslinking when cell carrier particles are made from natural gelatins, the degree of biodegradability is also variable. In applications such as cell delivery in medical applications this may impose a further imbalance in the healing process, so that in one place healing may proceed as intended, reaching full effect of treatment, while in other places beneficial effects may be impaired and may not go to completion. In case of tissue augmentation or plastic surgery an imbalanced biodegradability may cause the injected area to become irregular in shape, which is cosmetically unacceptable.

Now that according to the present invention particles with a uniform size and uniform properties can be made using recombinant gelatin polypeptides it is also possible to tune the biodegradation speed, and more important, to obtain a uniform biodegradation speed.

Thus, according to the invention with recombinant gelatins cell carrier particles can be produced that have more uniform properties than particles prepared from natural gelatin. The size distribution will be narrower. No extreme small or extreme large particles will be formed. Thus it can be expected that less than 10% of the particles in a population prepared from recombinantly produced gelatins will have a size that deviates more than 20% from the average size, and it can further be expected to have essentially no particles that deviate more than 50% from the average size. Preferably less than 5% of the particles have a size that deviates more than 20% from the average particle size. More preferably less than 5% of the particles have a size that deviates more than 10% from the average particle size. Most preferred is that less than 2.5% of the particles have a size that deviates more than 5% from the average particle size.

The cell carrier particles may be porous or non porous or may comprise cavities to increase the number of cells that can adhere, as described in for example WO 2003/104313.

Suitable gelatin polypeptides to make the recombinant cell carrier particles according to the invention are gelatins (or collagens) from recombinant sources. Although strictly speaking there is a difference between collagen and gelatin, these differences are in principle not essential to the invention, although specific requirements may make the selection of collagen or gelatin for a certain application obvious. In this respect "collagen" may also be read as "gelatin" and "collagen polypeptide" may also be read as "gelatin polypeptide". A gelatin or collagen or collageneous or gelatineous polypeptide is thus defined as being a polypeptide in which at least one GXY domain is present of at least a length of 5 consecutive GXY triplets and at least 20% of the amino acids of the gelatineous polypeptide are present in the form of consecutive GXY triplets, wherein a GXY triplet consists of G representing glycine and X and Y representing any amino acid. Suitably at least 5% of X and/or Y can represent proline and in particular at least 5%, more in particular between 10 and 33% of the amino acids of the GXY part of the collageneous polypeptide is proline.

The gelatineous polypeptide preferably has an average molecular weight of less than 150 kDa, preferably of less than 100 kDa. Ranges of between 50 and 100 kDa are suitable or gelatineous polypeptides of less than 75 kDa but more than 20 kDa or between 5 and 40 kDa may be used. Preferably the collageneous polypeptides have an average molecular weight of at least 5 kDa, preferably at least 10 kDa and more preferably of at least 30 kDa. Lower molecular weights may be preferred when higher concentrations of gelatineous polypeptides are required because of the lower viscosity.

The method of making recombinant gelatineous polypeptides has been described in detail in patent applications EP 0 926 543 and EP 1 014 176 by the same applicant, the content of which is herein incorporated by reference. The methodology is described in the publication 'High yield secretion of recombinant gelatins by Pichia pastoris', M. W. T. Werten et al., Yeast 15, 1087-1096 (1999). Suitable recombinant gelatins are also described in WO 2004/85473.

In one embodiment the recombinant gelatineous polypeptide does not form stable triple helices, specifically not at temperatures of higher than 5 degrees Celsius, or at temperatures higher than 25 degrees Celsius. Such gelatineous polypeptides have preferably an amount of prolines present in GXY triplets that is comparable to collagen or gelatin originating from mammals or collagens originating from cold-blooded animals such as fish. To prevent stable triple helix formation less than 2 number percent, preferably less than 1 number percent, of the amino acids present in the gelatineous polypeptide are hydroxylated. Occurrence of hydroxyprolines can be reduced to be practically zero by expression in micro organisms that do not co-express a prolylhydroxylase or fulfill that function in another way. Practically zero means that the presence of hydroxyprolines in the growth medium of for example yeasts may result in incorporation of some of these amino acids into the gelatineous polypeptide. Recombinant gelatineous polypeptides that are not hydroxylated and have the advantage of avoiding the occurrence of anaphylactic shock are described in EP 1 238 675.

In a preferred embodiment the cell carrier particles comprise gelatineous polypeptides with excellent cell attachment properties, and which do not display any health related risks Advantageously this is achieved by production of RGD-enriched gelatineous polypeptides in which the percentage of RGD motifs related to the total number of amino acids is at least 0.4. If the RGD-enriched gelatineous polypeptide comprises 350 amino acids or more, each stretch of 350 amino acids contains at least one RGD motif. Preferably the percentage of RGD motifs is at least 0.6, more preferably at least 0.8, more preferably at least 1.0, more preferably at least 1.2 and most preferably at least 1.5.

A percentage RGD motifs of 0.4 corresponds with at least 1 RGD sequence per 250 amino acids. The number of RGD motifs is an integer, thus to meet the feature of 0.4%, a gelatineous polypeptide consisting of 251 amino acids should comprise at least 2 RGD sequences. Preferably the RGD-enriched recombinant gelatineous polypeptide comprises at least 2 RGD sequence per 250 amino acids, more preferably at least 3 RGD sequences per 250 amino acids, most preferably at least 4 RGD sequences per 250 amino acids. In a further embodiment an RGD-enriched gelatineous polypeptide comprises at least 4 RGD motifs, preferably at least 6, more preferably at least 8, even more preferably at least 12 up to and including 16 RGD motifs.

The term 'RGD-enriched gelatineous polypeptide' in the context of this invention means that the gelatineous polypeptides have a certain level of RGD motifs, calculated as a percentage of the total number of amino acids per molecule and a more even distribution of RGD Natural gelatins are known to comprise RGD sequences. Only a fraction of the polypeptides in a natural hydrolyzed gelatin will have an RGD sequence. It is important however that a recombinant particle does not contain too large parts without RGD motifs. Too large parts without RGD sequence reduce the possibility of cell attachment. Apparently not all RGD sequences in a gelatineous polypeptide are under all circumstances available for cell attachment. It was found that cell attachment was remarkably improved in gelatineous polypeptides according to the invention comprising at least one RGD motif in each stretch of 350 amino acids when compared to gelatins having a stretch of amino acids of more than 350 without an RGD sequence. For gelatineous polypeptides of less than 350 amino acids it is sufficient to have a percentage of RGD sequences of at least 0.4.

Recombinant gelatineous polypeptides used in this invention are preferably derived from collageneous sequences. Nucleic acid sequences encoding collagens have been generally described in the art. (See, e. g., Fuller and Boedtker (1981) Biochemistry 20: 996-1006; Sandell et al. (1984) J Biol Chem 259: 7826-34; Kohno et al. (1984) J Biol Chem 259: 13668-13673; French et al. (1985) Gene 39: 311-312; Metsaranta et al. (1991) J Biol Chem 266: 16862-16869; Metsaranta et al. (1991) Biochim Biophys Acta 1089: 241-243; Wood et al. (1987) Gene 61: 225-230; Glumoff et al. (1994) Biochim Biophys Acta 1217: 41-48; Shirai et al. (1998) Matrix Biology 17: 85-88; Tromp et al. (1988) Biochem J 253: 919-912; Kuivaniemi et al. (1988) Biochem J 252: 633640; and Ala-Kokko et al. (1989) Biochem J 260: 509-516.).

For pharmaceutical and medical uses, recombinant gelatineous polypeptides with amino acid sequences closely related to or identical to amino acid sequences of natural human collagens are preferred. More preferably the amino acid sequence of the gelatineous polypeptide is designed by a repetitive use of a selected amino acid sequence of a human collagen. A part of a natural collagen sequence comprising an RGD motif is selected. The percentage of RGD motifs in such a selected sequence depends on the chosen length of the selected sequence, selection of a shorter sequence results in a higher RGD percentage. Repetitive use of a selected amino acid sequence results in a gelatin with a higher molecular weight, which is non-antigenic and with an increased number of RGD motifs (compared to natural gelatins or collagens).

Thus in a preferred embodiment the recombinant gelatineous polypeptide comprises a part of a native human collagen sequence. Preferably the RGD-enriched gelatineous polypeptide consists for at least 80% of one or more parts of one or more native human collagen sequences. Preferably each of such parts of human collagen sequences has a length of at least 30 amino acids, more preferably at least 45 amino acids, most preferably at least 60 amino acids, up to e.g. 240, preferably up to 150, most preferably up to 120 amino acids, each part preferably containing one or more RGD sequences. Preferably the RGD-enriched gelatineous polypeptide consists of one or more parts of one or more native human collagen sequences.

An example of a suitable source of a gelatineous polypeptide for preparing the recombinant particles according to this invention is human COL1A1-1. A part of 250 amino acids comprising an RGD sequence is given in WO 04/85473. RGD sequences in collageneous polypeptides can adhere to specific receptors on the cell wall called integrins. These integrins differ in their specificity in recognizing cell binding amino acid sequences. Although both natural gelatin and, for example, fibronectin may contain RGD sequences, gelatin can bind cells that will not bind to fibronectin and vice versa. Therefore fibronectin comprising RGD sequences cannot always replace gelatin for cell adhesion purposes.

As already mentioned RGD-enriched gelatineous polypeptides can be produced by recombinant methods as disclosed in EP-A-0926543, EP-A-1014176 or WO 01/34646. For the production and purification of gelatineous polypeptides that are suited for preparing cell carrier particles of this invention reference is made to the examples in EP 0 926 543 and EP 1 014 176. The preferred method for producing an RGD-enriched gelatineous polypeptides is by starting with a natural nucleic acid sequence encoding a part of the collagen protein that includes an RGD amino acid sequence. By repeating this sequence an RGD-enriched gelatineous polypeptide is obtained.

If X-RGD-Y (SEQ ID NO: 3) is a part of the natural collagen amino acid sequence, a (part of a) gelatineous polypeptide with three RGD amino acid sequences would have the structure -X-RGD-Y-(GXYG)m-X-RGD-Y-(GXYG)n-X-RGD-Y- (SEQ ID NO: 4), with m and n being integers starting from 0. By varying n the number of RGD sequences on the total amino acids the percentage of RGD motifs can be controlled. A clear advantage of this method is that the amino acid sequence remains most natural and thus has the lowest risk of inducing immunological response in clinical applications.

Starting from a natural nucleic acid sequence encoding (part of) a gelatineous polypeptide, also point mutations can be applied so as to yield a sequence encoding an RGD sequence. Based on the known codons a point mutation can be performed so that an RGX sequence after mutation will yield an RGD sequence, alternatively also an YGD sequence can be mutated to yield an RGD sequence. Also it is possible to carry out two mutations so that an YGX sequence will give an RGD sequence. Also it may be possible to insert one or more nucleotides or delete one or more nucleotides giving rise to a desired RGD sequence.

Thus the gelatineous polypeptides can be produced by expression of nucleic acid sequence encoding such polypeptide by a suitable micro-organism. The process can suitably be carried out with a fungal cell or a yeast cell. Suitably the host cell is a high expression host cells like Hansenula, Trichoderma, Aspergillus, Penicillium, Saccharomyces, Kluyveromyces, Neurospora or Pichia. Fungal and yeast cells are preferred to bacteria as they are less susceptible to improper expression of repetitive sequences. Most preferably the host will not have a high level of proteases that attack the collagen structure expressed. In this respect Pichia or Hansenula offers an example of a very suitable expression system. Use of Pichia pastoris as an expression system is disclosed in EP 0 926 543 and EP 1 014 176. The microorganism may be free of active post-translational processing mechanism such as in particular hydroxylation of proline and also hydroxylation of lysine. Alternatively the host system may have an endogenic proline hydroxylation activity by which the gelatineous polypeptide is hydroxylated in a highly effective way. The selection of a suitable host cell from known industrial enzyme producing fungal host cells specifically yeast cells on the basis of the required parameters described herein rendering the host cell suitable for expression of gelatineous polypeptides which are suitable for use as artificial skin in combination with knowledge regarding the host cells and the sequence to be expressed will be possible by a person skilled in the art.

In another embodiment the recombinant gelatineous polypeptides for making cell carrier particles have a higher glass transition temperature than natural occurring gelatins. Such sequences are described in WO 05/11740.

In a further embodiment, the gelatins used to make the cell carrier particles are low in glycosylation. There are various methods for ensuring that glycosylation is low or absent. Glycosylation is a posttranslational modification, whereby carbohydrates are covalently attached to certain amino acids of the protein or polypeptide. Thus both the amino acid sequence and the host cell (and enzymes, especially glycosyltransferases, therein) in which the amino acid sequence is produced determine the glycosylation pattern. There are two types of glycosylation: N-glycosylation begins with linking of GlcNAc (N-actylglucosamine) to the amide group of asparagines (N or Asn) and 0-glycosylation commonly links GalNAc (N-acetylgalactosamine) to the hydroxyl group of the amino acid serine (S or Ser) or threonine (T or Thr).

Glycosylation can, therefore, be controlled and especially reduced or prevented, by choosing an appropriate expression host, and/or by modifying or choosing sequences which lack consensus sites recognized by the hosts glycosyltransferases. Obviously, chemical synthesis of proteins or polypeptides results in unglycosylated proteins. Also, glycosylated proteins may be treated after production to remove all or most of the carbohydrates or unglycosylated proteins may be separated from glycosylated proteins using known methods.

In yeasts N-linked glycosylation of asparagine occurs on the consensus sites Asn-X-Thr or Asn-X-Ser, wherein X is an amino acid. Commonly glycosylation in yeast results in N-linked and O-linked oligosaccharides of mannose. Thus, for expression in yeast the nucleic acid sequence may be modified or selected so that consensus sites are reduced or preferably absent. The Asn codon and/or the Thr codon may be modified, e.g. by mutagenesis or de novo synthesis. Preferably Asn and/or Thr is replaced by another amino acid. Also Asp may be replaced by another amino acid. In one embodiment the polypeptide sequence contains no Ser and/or no Asn.

To analyze the degree of post-translational modification or to determine the content of glycosylation mass spectrometry, such as MALDI-TOF-MS (Matrix Assisted Laser Desorption Ionization mass spectrometry) can be carried out as known in the art.

Alternatively the amount of glycosylation can be determined using the titration method described by Michel Dubois et al, "Colorimetric Method for Determination of Sugars and Related Substances", Analytical Chemistry, vol 28, No. 3, March 1956, 350 356. This method can be used to determine simple sugars, oligosaccharides, polysaccharides, and their derivatives, including the methyl ethers with free or potentially free reducing groups.

The content of glycosylation of the gelatineous polypeptide used is preferably equal to, or less than about 2 (m/m) %, more preferably less than about 1 (m/m) %, most preferably less than about 0.5 (m/m) %, 0.2 (m/m) % or 0.1 (m/m) %. In a preferred embodiment the degree of glycosylation is zero.

The degree of glycosylation refers to the total carbohydrate weight per unit weight of the collageneous polypeptides as determined by for example MALDI-TOF-MS (Matrix Assisted Laser Desorption Ionization mass spectrometry) or the titration method by Dubois referred to above. The term 'glycosylation' refers not only to monosaccharides, but also to polysaccharides such as di- tri- or tetra saccharides.

Cells that can be adhered and/or grown on recombinant particles of the invention can be any living, genetically modified or malignant living cell. Preferred are human (or mammalian) cells such as fibroblasts, keratinocytes, melanocytes, Langerhans' cells, myocardiocytes and the like. In a preferred embodiment the cells are obtained from the subject to be treated.

In one embodiment, the particles contain no RGD-motifs. These can be used in cases where a-selective attachment of cells occurs, or where attachment is not dependent of RGD-sequences. Competition from RGD-anchorage depending cells can be avoided on such particles, which is not possible with particles made from a natural gelatin. Preferably such particles are macroporous particles.

The recombinant gelatin polypeptide may further comprise one or more bioactive compounds such as hormones, growth promoters, antibiotics, immune-suppressors, and the like. Further the cell carrier particles may comprise one or more compounds that can aid in wound healing processes. A "bioactive compound" is any compound (either a natural compound or a synthetic compound) which exerts a biological effect on other cells. Such compounds are widely available in the art. The compound may be incorporated in the particles during its manufacture or, alternatively, it may be added subsequently to the particles. In one embodiment two cell carrier batches comprising recombinant particles are provided in which each cell carrier batch carries a different cell or bioactive compound which can be injected after mixing said two batches or which can be injected subsequently.

The cell carrier particles can have an average size of from 1 to 500 micron.

In one embodiment the particles are suitable as injectable cell carriers and have an average particle size of less than or equal to 200 μm, e.g. between 10 and 200 μm, or between 10 and 175 μm, or between 10 and 150 μm or between 10 and 125 μm. Alternatively such particles have an average particle size of less than or equal to 100 μm, e.g. between 10 and 75 μm. Injectable cell carriers can for example be applied for delivery of tissue repairing cells without the need of invasive surgery such as the delivery of myocardiocytes in myocardial scar tissue.

In another embodiment the particles are suitable as injectable tissue fillers or for tissue augmentation or plastic surgery or cosmetic surgery. For such applications the average particle size is preferably more than or equal to 100 μm. Average particle sizes of 150 to 500 are also preferred. Other suitable average particle sizes are 220, 250, 300, 350, 400 and 450 μm. Particles suitable as tissue fillers or augmenters should be deformable so that no lump formation occurs, but a natural impression is obtained after injection of the particles.

In yet another embodiment the recombinant collagen particles are suitable as porous or non-porous microcarriers for in vitro cell cultures. Preferably microcarriers have an average size of between 100 and 200 μm. Such microcarriers are well known in the art and are described in for example WO 2003/104313, WO 90/13625, SU 1738851, SU 1321748 and in "Pure gelatin microcarriers: synthesis and use in cell attachment and growth of fibroblasts and endothelial cells"— (Wisseman et al, In Vitro (1985) 21, 7, 391-401).

In one embodiment the cell carrier batch comprises a monodisperse recombinant particle population. In another embodiment the cell carrier is a mix of two or more monodisperse recombinant particle populations, each population having a different average size.

The particles according to the invention can be prepared from recombinant gelatin with methods known in the art in which particles are formed out of a starting solution of the recombinant gelatin. Such methods comprise particle formation using oil/water emulsion techniques which may comprise phase inversion such as described in for example EP 222 718 or WO 2003/104313 or precipitation techniques such as described in for example SU 1161548.

EXAMPLES

Example 1

Preparation of Gelatin Based Cell Carrier Particles by Precipitation in Acetone A volume of 20 ml of a 2% aqueous solution of a recombinant gelatin (SEQ ID NO 1, 21 kDa) was added, while stirring, to 50 ml of acetone to which 0.1 ml of a 25% solution of N-(3-Dimethylaminopropyl)-N'-ethylcarbodiimide (EDC) had been added. The turbid dispersion was left standing without stirring for 10 minutes. The mixture was quenched in 500 ml of water. The particles were washed from remaining EDC and acetone by 3 cycles of centrifugation and resuspension in water. Finally the particles were dried in vacuo. Particles with an average size of approximately 20 μm were obtained (microscopic analysis).

In a similar way particles were produced with a recombinant gelatin containing an RGD-motif (SEQ ID NO 2, 24 kDa)

For comparison, particles were prepared according to the method described above using a hydrolyzed limed bone gelatin with an average molecular weight of 21 kDa.

Visual comparison learned that the particles prepared from recombinant gelatin were having a more uniform size, i.e. are significantly more monodisperse.

Example 2

Comparison of Cell Attachment

Cell Types and Culture Conditions

Green monkey kidney (Vero) cells, Chinese hamster ovary (CHO) cells, normal rat kidney fibroblast (NRK-49F) cells, and Madin Darby canine kidney (MDCK) cells were purchased from ATCC. All four cell types were passaged and maintained in 75 cm$@2$ flasks at 37 DEG C. in a 5% CO2 environment. Vero and NRK-49F cells were cultured in Dulbecco's Modified Eagle's Medium (DMEM), CHO cells were cultured in Ham's F-12 Nutrient Mixture, and MDCK cells were cultured in Minimum Essential Medium (MEM) with Earle's salts.

With the Vero and CHO cells, the medium was supplemented with 10% fetal bovine serum (FBS), 2 mM L-glutamine, 20 mM HEPES buffer, 1 mM sodium pyruvate, 100 μg/ml streptomycin, and 100 units/ml penicillin (final pH 7.1). With the NRK-49F cells, the DMEM was supplemented with 5% FBS, 2 mM L-glutamine, 1 mM sodium pyruvate, non-essential amino acids (0.1 mM each), 100 μg/ml streptomycin, 100 units/ml penicillin, and 0.25 μg/ml of amphotericin B (final pH 7.1). With the MDCK cells, the MEM was supplemented with 10% FBS, 2 mM L-glutamine, non-essential amino acids (0.1 mM each), and 100 μg/ml streptomycin, 100 units/ml penicillin, and 0.25 μg/ml of amphotericin B (final pH 7.1).

In order to standardize the physiology of cells prior to each experiment, cells were passed into 150 cm$@2$ flasks 2 to 3 days prior to inoculation of microcarrier beads. Cells were trypsinised (0.05% trypsin, 0.53 mM EDTA in PBS) for removal from the flasks. For the microcarrier experiments, the cells were centrifuged to remove the trypsin medium and resuspended to about 1 times 10$@6$ cells/ml in culture medium. The viable cell concentration was determined by Trypan dye exclusion (0.4% Trypan blue in 0.9% saline).

Cell Culture and Assays in Spinner Flasks

For the cell attachment assay, 20 mg/ml of cell carrier particles were used and the cell concentration was 1.5 times 10$@5$ cells/ml for each cell type.

Cell carrier particles were cultured with 100 ml cultures being maintained in 250 ml spinner vessels and stirred with suspended magnetic impellers (50 rpm).

The kinetics of cell attachment were assayed as a decrease in supernatant cell concentration. For sample removal the agitation was stopped briefly (about 30 seconds) at which time the cell carrier particles settled and a supernatant sample was removed for cell quantitation as described below.

For the cell counts, the cells were stained by mixing with an equal volume of crystal violet (0.1% w/w) in 0.1 M citric acid, and then counted with a hemocytometer. Cell depletion from the medium was used as an indicator of cells attached to beads To verify that cells removed from the medium were indeed attached to cell carrier particles (and not lysed), cells attached to cell carrier particles were quantitated at the end of each cell attachment assay. One ml aliquots of well-agitated carrier medium were removed, the microcarriers were allowed to settle, and the settled cell carrier particles were resuspended in crystal violet/citric acid as described above. After incubating 1 hour at 37 DEG C., the suspension was sheared by sucking into and out of a Pasteur pipette to release nuclei, which were quantitated with a hemocytometer.

With the above method the conventional gelatin particles were compared to the particles made from recombinantly produced gelatin containing an RGD-motif (SEQ ID NO 2). Although the percentage of RGD motifs in the starting material for preparing the cell carrier particles is the same (both 0.8 percent), the particles made from the recombinant collagen gave a much better cell attachment. This is attributed to the more uniform presence of RGD and the better distribution thereof in the recombinant collagen.

The invention claimed is:

1. A cell carrier particle comprising crosslinked recombinantly produced gelatin polypeptides, wherein said recombinantly produced gelatin polypeptides comprise at least two outer lysine residues and wherein said outer lysine residues are separated by at least 25 percent of the total number of amino acids in the recombinant gelatin polypeptide.

2. The cell carrier particle according to claim 1, wherein the recombinantly produced gelatin polypeptides comprise at least one lysine residue between said outer lysine residues.

3. The cell carrier particle according to claim 1, wherein the recombinantly produced gelatin polypeptides further comprise at least two outer aspartic acid and/or glutamic acid residues and wherein said outer aspartic acid and/or glutamic acid residues are separated by at least 25 percent of the total number of amino acids in the recombinant gelatin polypeptide.

4. The cell carrier particle according to claim 3, wherein the recombinantly produced gelatin polypeptides comprise at least one aspartic acid residue or glutamic acid residue between said first and second aspartic acid residues and/or glutamic acid residues.

5. The cell carrier particle according to claim 1, wherein at least on of the lysine residues is cross linked to at least one aspartic acid and/or glutamic acid residue.

6. The cell carrier particle according to claim 5, wherein the recombinantly produced gelatin polypeptides are crosslinked using 1-ethyl-3-(3-dimethylaminopropyl)carbodiimide (EDC).

7. The cell carrier particle according to claim 1, wherein each stretch of 50 amino acids of said recombinantly produced gelatin polypeptides comprises at least two lysine residues.

8. The cell carrier particle according to claim 1, wherein each stretch of 50 amino acids of said recombinantly produced gelatin polypeptides comprises at least one amino acid residue independently selected from aspartic acid or glutamic acid.

9. The cell carrier particle according to claim 1, wherein less than 10 percent of said particles have a size that deviates more than 20 percent from the average size of said particles.

10. The cell carrier particle according to claim 1, wherein essentially no particles are present that deviate more than 50 percent from the average size of said particles.

11. The cell carrier particle according to claim 1, wherein the recombinantly produced gelatin polypeptides comprise at least one RGD motif.

12. The cell carrier particle according to claim 11, wherein the percentage of RGD-motifs related to the total number of amino acids in the RGD-motif-containing recombinantly produced gelatin polypeptide is at least 0.4 and if said gelatin polypeptide comprises 350 amino acids or more, each stretch of 350 amino acids contains at least one RGD-motif.

13. The cell carrier particle according to claim 12, wherein the percentage of RGD-motifs related to the total number of amino acids in the RGD-motif-containing recombinantly produced gelatin polypeptide is at least 0.6.

14. The cell carrier particle according to claim 1, wherein the molecular weight of said recombinantly produced gelatin polypeptides is between 2.5 kDa and 150 kDa.

15. A method of delivering cells to a subject comprising injecting cells adhered and/or grown on a cell carrier particle according to claim 1, wherein said particles have an average particle size of less than or equal to 200 µm.

16. The method according to claim 15, wherein said cells are myocardiocytes which are delivered at myocardial scar tissue sites.

17. A method of culturing cells in vitro comprising incubating cells in the presence of a cell carrier particle according to claim 1.

18. The cell carrier particle according to claim 13, wherein the percentage of RGD-motifs related to the total number of amino acids in the RGD-motif-containing recombinantly produced gelatin polypeptide is at least 0.8.

19. The cell carrier particle according to claim 18, wherein the percentage of RGD-motifs related to the total number of amino acids in the RGD-motif-containing recombinantly produced gelatin polypeptide is at least 1.0.

20. The cell carrier particle according to claim 19, wherein the percentage of RGD-motifs related to the total number of amino acids in the RGD-motif-containing recombinantly produced gelatin polypeptide is at least 1.2.

21. The cell carrier particle according to claim 20, wherein the percentage of RGD-motifs related to the total number of amino acids in the RGD-motif-containing recombinantly produced gelatin polypeptide is at least 1.5.

22. The cell carrier particle according to claim 14, wherein the molecular weight of said recombinantly produced gelatin polypeptides is between 10 kDa and 100 kDa.

23. The cell carrier particle according to claim 22, wherein the molecular weight of said recombinantly produced gelatin polypeptides is between 20 and 75 kDa.

* * * * *

SEQUENCE LISTING

<160> NUMBER OF SEQ ID NOS: 4

<210> SEQ ID NO 1
<211> LENGTH: 209
<212> TYPE: PRT
<213> ORGANISM: Artificial sequence

```
<220> FEATURE:
<223> OTHER INFORMATION: Description of Artificial Sequence: Synthetic
      recombinant gelatin sequence

<400> SEQUENCE: 1

Gly Pro Pro Gly Glu Pro Gly Pro Thr Gly Leu Pro Gly Pro Pro Gly
1               5                   10                  15

Glu Arg Gly Gly Pro Gly Ser Arg Gly Phe Pro Gly Ala Asp Gly Val
            20                  25                  30

Ala Gly Pro Lys Gly Pro Ala Gly Glu Arg Gly Ser Pro Gly Pro Ala
        35                  40                  45

Gly Pro Lys Gly Ser Pro Gly Glu Ala Gly Arg Pro Gly Glu Ala Gly
    50                  55                  60

Leu Pro Gly Ala Lys Gly Leu Thr Gly Ser Pro Gly Ser Pro Gly Pro
65                  70                  75                  80

Asp Gly Lys Thr Gly Pro Pro Gly Pro Ala Gly Gln Asp Gly Arg Pro
            85                  90                  95

Gly Pro Pro Gly Pro Pro Gly Ala Arg Gly Gln Ala Gly Val Met Gly
            100                 105                 110

Phe Pro Gly Pro Lys Gly Ala Ala Gly Glu Pro Gly Lys Ala Gly Glu
            115                 120                 125

Arg Gly Val Pro Gly Pro Pro Gly Ala Val Gly Pro Ala Gly Lys Asp
130                 135                 140

Gly Glu Ala Gly Ala Gln Gly Pro Pro Gly Pro Ala Gly Pro Ala Gly
145                 150                 155                 160

Glu Arg Gly Glu Gln Gly Pro Ala Gly Ser Pro Gly Phe Gln Gly Leu
            165                 170                 175

Pro Gly Pro Ala Gly Pro Pro Gly Glu Ala Gly Lys Pro Gly Glu Gln
            180                 185                 190

Gly Val Pro Gly Asp Leu Gly Ala Pro Gly Pro Ser Gly Pro Ala Gly
            195                 200                 205

Gly

<210> SEQ ID NO 2
<211> LENGTH: 252
<212> TYPE: PRT
<213> ORGANISM: Artificial sequence
<220> FEATURE:
<223> OTHER INFORMATION: Description of Artificial Sequence: Synthetic
      recombinant gelatin sequence containing 2
      RGD-motifs

<400> SEQUENCE: 2

Gly Ala Pro Gly Ser Gln Gly Ala Pro Gly Leu Gln Gly Met Pro Gly
1               5                   10                  15

Glu Arg Gly Ala Ala Gly Leu Pro Gly Pro Lys Gly Asp Arg Gly Asp
            20                  25                  30

Ala Gly Pro Lys Gly Ala Asp Gly Ser Pro Gly Lys Asp Gly Val Arg
        35                  40                  45

Gly Leu Thr Gly Pro Ile Gly Pro Pro Gly Ala Gly Ala Pro Gly
    50                  55                  60

Ala Pro Gly Ser Gln Gly Ala Pro Gly Leu Gln Gly Met Pro Gly Glu
65                  70                  75                  80

Arg Gly Ala Ala Gly Leu Pro Gly Pro Lys Gly Asp Arg Gly Asp Ala
            85                  90                  95

Gly Pro Lys Gly Ala Asp Gly Ser Pro Gly Lys Asp Gly Val Arg Gly
            100                 105                 110
```

```
Leu Thr Gly Pro Ile Gly Pro Pro Gly Pro Ala Gly Ala Pro Gly Ala
        115                 120                 125
Pro Gly Ser Gln Gly Ala Pro Gly Leu Gln Gly Met Pro Gly Glu Arg
    130                 135                 140
Gly Ala Ala Gly Leu Pro Gly Pro Lys Gly Asp Arg Gly Asp Ala Gly
145                 150                 155                 160
Pro Lys Gly Ala Asp Gly Ser Pro Gly Lys Asp Gly Val Arg Gly Leu
            165                 170                 175
Thr Gly Pro Ile Gly Pro Pro Gly Pro Ala Gly Ala Pro Gly Ala Pro
        180                 185                 190
Gly Ser Gln Gly Ala Pro Gly Leu Gln Gly Met Pro Gly Glu Arg Gly
    195                 200                 205
Ala Ala Gly Leu Pro Gly Pro Lys Gly Asp Arg Gly Asp Ala Gly Pro
    210                 215                 220
Lys Gly Ala Asp Gly Ser Pro Gly Lys Asp Gly Val Arg Gly Leu Thr
225                 230                 235                 240
Gly Pro Ile Gly Pro Pro Gly Pro Ala Gly Ala Pro
            245                 250

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 3

Xaa Arg Gly Asp Tyr
1               5

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (19)..(19)
<223> OTHER INFORMATION: Any amino acid
```

```
<400> SEQUENCE: 4

Xaa Arg Gly Asp Tyr Gly Xaa Tyr Gly Xaa Arg Gly Asp Tyr Gly Xaa
1               5                   10                  15

Tyr Gly Xaa Arg Gly Asp Tyr
            20
```